(12) United States Patent
Decout et al.

(10) Patent No.: US 7,220,543 B2
(45) Date of Patent: May 22, 2007

(54) METHOD AND SUPPORT FOR BIOLOGICAL ANALYSIS USING OLIGONUCLEOTIDES COMPRISING A MARKER CAPABLE OF ENZYMATIC ACTIVATION

(75) Inventors: Jean-Luc Decout, Vaulnaveys-le-Haut (FR); Marc Fontecave, Saint Ismien (FR); Cécile Dueymes, Rodez (FR)

(73) Assignees: Commissariat a l'Energie Atomique, Paris (FR); Universite Joseph Fourier (UJF), Grenoble Cedex (FR)

( * ) Notice: Subject to any disclaimer, the term of this patent is extended or adjusted under 35 U.S.C. 154(b) by 545 days.

(21) Appl. No.: 10/484,178

(22) PCT Filed: Jul. 12, 2002

(86) PCT No.: PCT/FR02/02482

§ 371 (c)(1),
(2), (4) Date: Jan. 15, 2004

(87) PCT Pub. No.: WO03/008641

PCT Pub. Date: Jan. 30, 2003

(65) Prior Publication Data

US 2005/0042610 A1 Feb. 24, 2005

(30) Foreign Application Priority Data

Jul. 16, 2001 (FR) .................. 01 09460

(51) Int. Cl.
*C12Q 1/68* (2006.01)
*C07H 21/02* (2006.01)
*C07H 21/04* (2006.01)

(52) U.S. Cl. .......... 435/6; 536/23.1; 536/24.3

(58) Field of Classification Search .......... 435/6; 536/23.1, 24.3
See application file for complete search history.

(56) References Cited

U.S. PATENT DOCUMENTS

| 4,725,537 A | * | 2/1988 | Fritsch et al. ............. 435/6 |
| 4,743,535 A | * | 5/1988 | Carrico ................. 435/6 |
| 4,959,309 A | | 9/1990 | Dattagupta et al. |
| 5,482,832 A | | 1/1996 | Lens et al. |
| 5,624,813 A | * | 4/1997 | Mahant .............. 435/28 |
| 5,925,525 A | | 7/1999 | Fodor et al. |

FOREIGN PATENT DOCUMENTS

EP 0 097 373 A2 1/1984
EP 0 461 731 A2 12/1991
WO WO 01/63282 A2 8/2001

OTHER PUBLICATIONS

Structure of FAD (Flavin Adenine dinucleotide) at http://serva.de/products /data/21490.02.shtml.*
Fieschi, Franck et al., "The Mechanism and Substrate Specificity of the NADPH:Flavin Oxidoreductase from *Escherichia coli*", The Journal of Biological Chemistry, vol. 270, No. 51: 30392-30400, Dec. 22, 1995.
Fisher, Jed et al., "Enzyme-Catalyzed Redox Reactions with the Flavin Analogues 5-Deazariboflavin, 5-Deazariboflavin 5'-Phosphate, and 5-Deazariboflavin 5'-Diphosphate, 5'→5'-Adenosine Ester", Biochemistry, vol. 15, No. 5: 1054-1064, 1976.
Frier, Christelle et al., "Method for Preparing New Flavin Derivatives: Synthesis of Flavin-Thymine Nucleotides and Flavin-Oligonucleotide Adducts", The Journal of Organic Chemistry, vol. 62, No. 11: 3520-3528, 1997.
Hastings, J. Woodland et al., "Biochemistry and Physiology of Bioluminescent Bacteria", Advances in Microbial Physiology, vol. 26: 235-291, 1985.
Scott, T. Gordon et al., "Emission Properties of NADH. Studies of Fluorescence Lifetimes and Quantum Efficiencies of NADH, AcPyADH, and Simplified Synthetic Models", Journal of the American Chemical Society, vol. 92, No. 3: 687-695, Feb. 11, 1970.
Zenno, Shuhei et al., "Identification of the Gene Encoding the Major NAD(P)H-Flavin Oxidoreductase of the Bioluminescent Bacterium *Vibrio fischeri* ATCC 7744", Journal of Bacteriology, vol. 176, No. 12: 3536-3543, Jun. 1994.

* cited by examiner

*Primary Examiner*—Ethan Whisenant
(74) *Attorney, Agent, or Firm*—Hutchison Law Group PLLC

(57) ABSTRACT

The invention concerns a method for analyzing biological targets of DNA or RNA type, which comprises the following steps:
a) contacting the targets to be analyzed (ICAM-20) with oligonucleotide probes (ISIS) labeled with a cofactor A of an enzyme E;
b) adding, to the reaction medium, enzyme E corresponding to cofactor A and a substrate S of enzyme E, substrate S being converted by enzyme E into a compound C;
c) measuring a signal representative of the activity of enzyme E on substrate S, for example the fluorescence intensity (I) of substrate S; and
d) comparing this signal with the signal obtained when the oligonucleotide probes labeled with cofactor A (ISIS) are contacted with enzyme E and substrate S, under the same conditions, but in the absence of the targets, the difference between the two signals indicating the presence of complementary targets (ICAM-20) of the oligonucleotide probes.

15 Claims, 3 Drawing Sheets

METHOD AND SUPPORT FOR BIOLOGICAL ANALYSIS USING OLIGONUCLEOTIDES COMPRISING A MARKER CAPABLE OF ENZYMATIC ACTIVATION

DESCRIPTION

1. Technical Field

The subject of the present invention is a method and analytical support for the determination of biological targets of DNA or RNA type. This support and method find applications in numerous areas, in particular in biology for sequencing genomes, the search for mutations, the development of new medicinal products, etc . . .

2. Prior Art

The methods and analytical supports of this type generally use a plurality of oligonucleotide probes able to give rise to hybridization with biological targets to be analyzed. Hybridization corresponds to the pairing of target strands with complementary DNA strands, i.e. the probes, arranged at precise coordinates on the support. To determine the nature of the targets, it is therefore necessary to be able to define which sites on the support and hence which oligonucleotides gave rise to hybridization.

In document U.S. Pat. No. 5,925,525 [1] hybridization of biological targets is determined on the support by means of a fluorescent marker associated with the biological targets. Therefore, after contacting the labeled targets with the analysis support comprising the oligoprobes, then washing, the sites on which hybridization took place are determined by conducting excitation of all the fluorescent markers, followed by location of the sites by detecting the fluorescent light re-emitted by the markers. The sites for which fluorescent light is detected are those which fixed target molecules.

This technique has the disadvantage of requiring the labeling of the biological target before it is contacted with the analysis support, which raises certain practical problems concerning the quantification and/or yield of labeling and the time delay required. Also, labeling at a given stage freezes the situation and prevents subsequent dynamic measurements to follow up a hybridization reaction.

Another technique for detecting and identifying a nucleic acid (target) by its hybridization capacity, described in U.S. Pat. No. 5,4484,832 [2] consists of labeling these probes with an enzyme, then of contacting the enzyme-labeled oligonucleotides with the targets. Separation of the non-hybridized oligonucleotides from the duplexes is made by gel electrophoresis. Detection and determination of hybridization, after migration, is made by staining the gel using an appropriate substrate.

This gel technique limits the number of tested targets and therefore requires the fixation of enzymes onto the oligonucleotide probes, which raises some problems and carries the risk, in some cases, of disturbing hybridization of the oligonucleotide with the complementary oligonucleotide.

DESCRIPTION OF THE DISCLOSURE

The subject of the invention is precisely a method and an analysis support for biological targets using probes carrying a marker that can be enzymatically activated, but which do not require fixation of an enzyme on oligonucleotide probes.

According to the invention, the method for analyzing biological targets of DNA or RNA type comprises the following steps:

a) contacting the targets to be analyzed with oligonucleotide probes labeled with a cofactor A of an enzyme E, the cofactor being such that it is recognized by enzyme E when it is fixed onto a free oligonucleotide and is less recognized by enzyme E when the oligonucleotide on which it is fixed is hybridized with a complementary oligonucleotide;

b) adding, to the reaction medium, enzyme E corresponding to cofactor A and a substrate S of enzyme E, substrate S being converted by enzyme E into a compound C;

c) measuring a signal representative of the activity of enzyme E on substrate S; and d) comparing this signal with the signal obtained when the oligonucleotide probes labeled with cofactor A are contacted with enzyme E and substrate S, under the same conditions, but in the absence of the targets, the difference between the two signals indicating the presence of complementary targets of the oligonucleotide probes.

In this method, benefit is drawn from the fact that cofactor A is less recognized by enzyme E when the oligonucleotide probes labeled with cofactor A are hybridized with complementary targets. On this account, the activity of enzyme E on substrate S drops when there is hybridization.

Preferably, to obtain a significant comparison of the enzymatic activity of enzyme E on substrate S, cofactor A is such that it is no longer or almost no longer recognized by enzyme E when the oligonucleotide probes labeled with cofactor A are hybridized with complementary biological targets.

Further preferably, the signal measured in step c) represents no more than 50% of the signal obtained in the absence of biological targets.

The present invention is therefore based on the principle according to which a signal is obtained which varies when hybridization of the labeled oligonucleotide with a complementary oligonucleotide occurs. In the case of the invention, the variation of this signal is based on the use of an enzyme E which triggers this signal both on the amplifying effect of the enzyme and on the intensity of this signal, which provides an improved signal to noise ratio.

To implement the method of the invention, a system: cofactor A, enzyme E and substrate S, is preferably chosen such that it allows detection of the drop in enzymatic activity by means of an optic signal.

This drop in activity can be detected by using a substrate S for example having light absorbing and/or specific fluorescence properties which are different from the light absorbing and/or fluorescence properties of compound C obtained by converting substrate S under the action of enzyme E.

It is also possible to detect this drop in enzyme activity, if compound C of substrate conversion has light absorbing and/or specific fluorescence properties, by measuring an optic signal representative of the quantity of compound C formed.

Therefore, in the absence of a complementary target oligonucleotide, enzyme E recognizes cofactor A fixed on the oligonucleotide probe and enzymatic activity can be measured after the oligonucleotide probe labeled with cofactor A has been placed in contact with enzyme E and substrate S. The enzymatic reaction corresponds to the following:

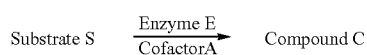

Should substrate S have maximum absorption at wavelength $\lambda_1$ or maximum fluorescence emission at wavelength $\lambda_2$ for which compound C has no light absorbing or fluorescence emitting properties, the enzymatic activity can be determined by the variation in optic density ($\Delta$OD) at wavelength $\lambda_1$ or by the variation of fluorescence ($\Delta$fluo) at wavelength $\lambda_2$ in relation to time.

When the oligonucleotide probe labeled with cofactor A is hybridized with a complementary target oligonucleotide, enzyme E no longer or almost no longer recognizes cofactor A, and substrate S is no longer or almost no longer converted into compound C. The result is that $\Delta$OD/min or $\Delta$fluo/min decreases.

Preferably a system: cofactor A, enzyme E, substrate S is used, such that this decrease represents from 50 to 100% of the maximum $\Delta$OD/min or $\Delta$fluo/min value obtained with the oligonucleotide probe labeled with A alone, i.e. with no complementary oligonucleotide.

Recognition of cofactor A fixed on the oligonucleotide probe by enzyme E varies in relation to the number of complementary bases present on the target oligonucleotide. As a result, a relation between $\Delta$OD/min and $\Delta$fluo/min exists which relates to this number of bases. This makes it possible to conduct a fine analysis of the extent of complementarity between the target oligonucleotide to be analyzed and the labeled oligonucleotide probe.

Also, detection of hybridizations can be obtained by measuring the variation of an optic signal (variation of OD or fluorescence) connected with the consumption of substrate S and generated by the action of an enzyme.

In addition, consumption of S and signal amplitude may be made substantial through the amplification effect due to the enzyme.

According to the invention, it is also important that the recognition process between cofactor A and enzyme E is not based on the formation of a covalent bond between these two elements, i.e. that cofactor A does not adhere covalent fashion to enzyme E so that this amplification effect can be obtained.

In one embodiment of the method of the invention, cofactor A is flavin or one of its derivatives.

Generally, these compounds are fixed on oligonucleotides by means of a spacer arm, for example of —(CH$_2$)$_n$— type to give flavin-oligonucleotide conjugates. A synthesis of conjugates of this type is described by C. Frier et al in J. Org. Chem., 62, 1997, p. 3520-3528 [3].

This synthesis consists of fixing a flavin derivative on the oligonucleotide using a phosphoramidite or H-phosphonate coupling method, starting with a derivative of formula:

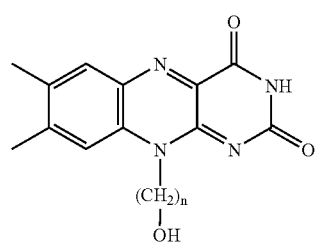

(I)

where n is a whole number from 2 to 8, for example 6.

Synthesis strategy enables insertion of the flavin group, including in automated oligonucleotide synthesis methods.

The oligonucleotide is consequently labeled with a group of formula —(CH$_2$)n-R$^1$ in which n is a whole number ranging from 2 to 8 and R$^1$ represents the group of formula:

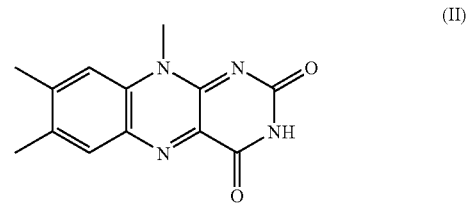

(II)

Enzymes E able to be used with this cofactor may be flavoproteins among which different oxidases are found. Preferably, in the invention, use is made of NAD(P)H oxidases and NAD(P)H: flavin oxidoreductases also called flavin reductases.

As an example of NAD(P)H oxidase, the one derived from yeast can be cited, called Old Yellow Enzyme and described by J. Fisher et al., Biochemistry, 1976, 15, p. 1054-1063 [4].

As an example of flavin reductase, mention can be made of the one described by F. Fieschi et al. in J. Bio. Chem., 1995, 270, p. 30392-30400 [5].

The substrates which can be used with these enzymes may be NADPH and NADH.

The use of flavins as cofactor is of great interest as they are molecules which act as cofactors of flavin reductases, i.e. soluble enzymes which catalyze the oxidation of NADPH or NADH by oxygen in the air following the schema:

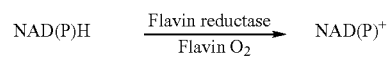

fluorescent at $\lambda_2$ = 460 nm     non-fluorescent
maximum absorption at $\lambda_1$ = 340 nm     no absorption In this schema, flavin reductase catalyzes the reduction of flavins by NAD(P)H. The reduced flavins produced by the reaction then react spontaneously with oxygen in the air to re-form flavins in their initial state. Numerous conversion cycles can be conducted in this manner enabling major consumption of NADPH or NADH. This phenomenon of enzymatic amplification allows substantial signals to be obtained.

In the invention, the use of NADPH or NADH as substrate is of particular interest since these molecules are endowed with characteristic light absorption and fluorescence emission which their oxidation products NADP$^+$ and NAD$^+$ do not have.

The fluorescence emission properties of NADH are particularly described by Scott et al in J. Am. Chem. Soc., 92:3, 11 Feb. 1970, p. 687 to 695 [6].

Hence, NADH has maximum fluorescence at wavelength 460 nm, and maximum absorption at wavelength 340 nm, whereas its conversion product with the NAD$^+$ enzyme has no fluorescence and no absorption.

Also, flavin oxireductase forms an excellent example of enzyme which may be used in the invention. It is a monomer protein, soluble, stable, easy to purify from an overproductive strain. The preparation of this enzyme is described in reference [5]. This enzyme exclusively recognizes the isoalloxazine cycle of flavin and can therefore use as cofactors a very wide range of flavin analogues having modifications on the ribityl chain such as described in reference [5].

According to the invention, it has been discovered that the flavin group fixed onto the oligonucleotide is recognized by flavin reductase so that the flavin-oligonucleotide conjugate always forms a cofactor enabling the enzyme to catalyze oxidation of NADPH or NADH and hence to trigger a reduction in light absorption at 340 nm and a reduction in fluorescence at 460 nm.

When flavin cofactor A is not in a saturating state relative to enzyme E concentration, OD variation in fluorescence (ΔOD or Δfluo) per unit of time is proportional to the quantity of flavin cofactor A. This allows quantification of cofactor A-labeled probes.

According to the invention, it has been found that when a flavin-oligonucleotide conjugate is hybridized to a complementary oligonucleotide, the flavin group is no longer recognized by flavin reductase which, on this account, is no longer able to catalyze oxidation of NADPH or NADH and to trigger a reduction in absorption at 340 nm and in fluorescence at 460 nm.

To conclude, without hybridization, the flavin-oligonucleotide probe (oligo-A) is detected by measuring a signal consisting of a decrease in optical density or fluorescence per unit of time or for a fixed time, 5 minutes for example. This signal tends towards partial or total extinction (ΔOD or Δfluo decreases or in the best of cases becomes zero) and specifically so when there is hybridization with a non-labeled complementary target. Evidence of hybridization can therefore be detected by variation in the reduction of optical density or fluorescence emission.

One advantage of this method is that this variation in the measured signal does not reflect the variation in optical density or fluorescence of a given molecule but of several molecules of substrate S of enzyme A using A as cofactor. The enzymatic reaction therefore enables considerable amplification of the response.

According to one variant of embodiment of the invention which can be used in the system: flavin (cofactor A) flavin reductase (enzyme E) and NADH or NADPH (substrate), a signal can be obtained that is representative of the enzymatic activity of enzyme E by using a second enzyme and an aldehyde, the second enzyme being able to catalyze the reaction of the flavin reduced with aldehyde and oxygen, this reaction being accompanied by luminescence representative of the activity of enzyme E. The second enzyme is luciferase for example, and the aldehyde may be decanal.

In a first step, as described previously, substrate S is converted into compound C by the first enzyme E (flavin reductase) forming reduced flavin. In a second step, the second enzyme (luciferase) catalyzes the reaction of reduced flavin with the aldehyde (RCHO) and oxygen, in accordance with the following reaction schema:

Reduced flavin+RCHO+O$_2$→RCOOH+oxidized flavin+(light)      (hν)

This corresponds to luminescence at 490 nm.

This reaction is particularly described by Hastings et al., Advances in Microbial Physiology, vol. 26, 1985, p. 235-291 [7] and by Zenno et al., J. Bacteriol., 1994, p. 3536-3543 [8].

The oxidized flavin so formed may be used by flavin reductase to convert substrate S and again be reduced.

Therefore, when the probe is hybridized with a complementary target, these reactions no longer occur and there is no more light. With the oligoflavin this therefore gives light when there is no hybridization and no longer gives light when there is hybridization.

Detection of hybridization by luminescence measurements is of interest since the signal is specifically connected with a chemical reaction and not with intrinsic properties (absorption or fluorescence) of objects (means) used.

We are therefore in the presence of something highly specific as the supports may be slightly fluorescent and this may affect fluorescence measurements. On the other hand, they are not chimioluminescent.

In this variant of the invention, the flavin reductase of *E. coli* or *V. harveyi* may be used, and the luciferase of *V. harveyi*.

In this case, to the probe labeled with flavin, flavin reductase and luciferase, is added decanal for example 0.001% vol/vol, 200 μM NADPH or NADH, and phosphate buffer, pH 7.50 mM. Luminescence is measured with a commercially available lumiphotometer at 490 nm. When this operation is repeated with a complementary target oligonucleotide, there is no luminescence.

According to the invention, the oligonucleotide probes labeled with cofactor A are preferably fixed onto a solid support. This solid support may be provided with microdishes in which the probes are fixed.

Therefore, a further subject of the invention is an analysis support for biological targets of DNA or RNA type comprising oligonucleotide probes fixed on a solid support, characterized in that the oligonucleotide probes are labeled with a cofactor A of an enzyme E such that cofactor A fixed on the probe is recognized by enzyme E, but is less recognized by enzyme E when the oligonucleotide probe is hybridized with a complementary oligonucleotide, enzyme E being such that it has a substrate S or a conversion compound C of this substrate which enables determination of the activity of enzyme E by an optic signal representative of the consumption of substrate S or of the production of compound C.

Preferably cofactor A is flavin or one of its derivatives.

Therefore the oligonucleotide probe may be labeled with a group of formula —(CH$_2$)n-R$^1$ in which n is a whole number ranging from 2 to 8 and R$^1$ represents a group meeting the formula:

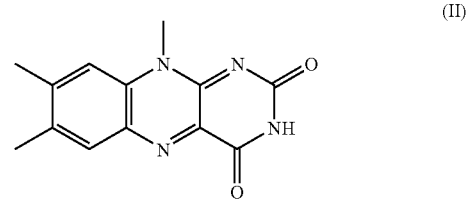

(II)

Other characteristics and advantages of the invention will become better apparent on reading the following description which is evidently given as an illustrative, non-restrictive example, with reference to the appended drawings.

SHORT DESCRIPTION OF THE DRAWINGS

DETAILED DESCRIPTION OF EMBODIMENTS

In the following examples, the following oligonucleotides are used:

```
1) flavin-oligonucleotide probe
ISIS:
3'-ctctcccctt caccacccc-p-C6flavin    SEQ ID N°: 1

2) complementary targets of the
flavin-oligonucleotide probe
ICAM-20:
5'-gcctgatgag aggggaagtg gtggggaga    SEQ ID N°: 2
catagcccca cc-3'

ICAM-17:
5'-gcctgatgag aggggaagtg gtggcccaga   SEQ ID N°: 3
catagcccca cc-3'

ICAM-14:
5'-gcctgatgag aggggaagtg gattcccaga   SEQ ID N°: 4
catagcccca cc-3'

3) non-complementary oligonucleotide
NC:
5'-ctcatcgtgt aaaaaaaaaa aggcagtact   SEQ ID N°: 5
ggaagggcta attct-3'
```

The ISIS flavin-oligonucleotide probe was synthesized using the method described in reference [6].

In these examples, flavin reductase is used as enzyme E, prepared following the method described in reference [8].

The fluorescence emission and excitation spectra were recorded on LS 50B Perkin-Elmer spectrofluorometer equipped with pulsed xenon source, an excitation monochromator, an emission monochromator and a temperature regulation system.

EXAMPLE 1

In this example, changes in enzymatic activity of flavin reductase are examined on the ISIS probe (SEQ I: N°1) in relation to increasing quantities of complementary target oligonucleotide ICAM-20 (SEQ. ID N°:2).

To the tank of a Varian-Cary spectrophotometer equipped with a temperature regulator, a total volume of 100 µl is added containing the following compounds: 50 mM Tris HCl buffer, pH 7.5, 10 mM NaCl, 10 µM ISIS probe, 200 µM NADH and 0.1 µm flavin reductase, and increasing quantities of ICAM-20 target oligonucleotide.

Initially, the double helix between ISIS and ICAM-20 is formed in the Tris buffer in the presence of NaCl, at room temperature, and the NADH is then added. The reaction is then set up by adding 0.1 µm flavin reductase (0.3 µm per assay). It is continued for a few minutes in air and at 25° C.

The oxidation of NADH is followed by electronic spectroscopy at 340 nm, the absorption wavelength characteristic of NADH.

Figure 1:
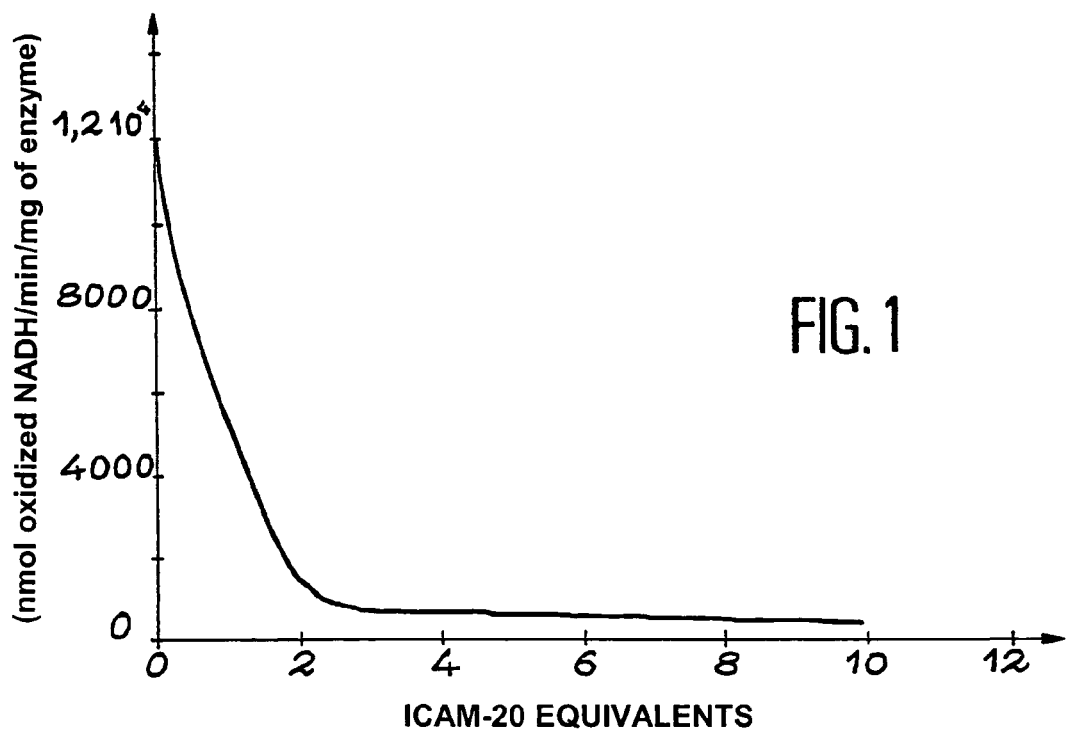
FIG. 1 is a curve illustrating changes in the enzymatic activity of flavin reductase in relation to increasing quantities of a complementary target oligonucleotide.

FIG. 1 shows the changes in enzymatic activity of flavin reductase (in nmol oxidized NADH min/mg of enzyme) in relation to the number of equivalents of target ICAM-20 present.

The results obtained in FIG. 1 show that that enzymatic activity decreases rapidly when the number of equivalents of target ICAM-20 increases.

EXAMPLE 2

In this example verification is made of the influence of the number of complementary bases of the target on measured enzymatic activity.

In this example, the same operating mode is followed as in example 1, but in addition the other target oligonucleotides are used consisting of ICAM-17 (SEQ. ID N°:3), ICAM-14 (SEQ. ID N°:4) and NC (SEQ. ID N°:5). In each case ten equivalents of the target oligonucleotides are used.

Enzymatic activity is determined as in example 1.

Figure 2:
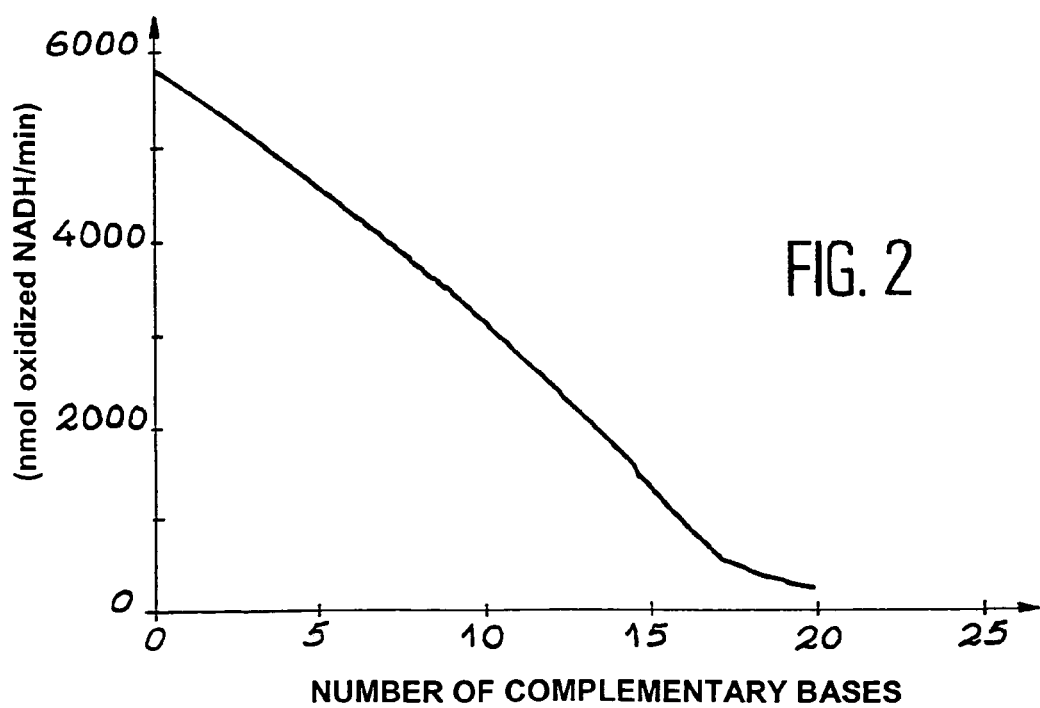
FIG. 2 illustrates enzymatic activity determined in relation to the number of complementary bases of the target oligonucleotide.

The results are given in table 1 and FIG. 2.

TABLE 1

|  | Enzyme activity nmol of oxidized NADH/min |
|---|---|
| Target ICAM-20: 20 complementary bases (SEQ. ID N°: 2) | 200 |
| Target ICAM-17: 17 complementary bases (SEQ. ID N°: 3) | 500 |
| Target ICAM-14: 14 complementary bases (SEQ. ID N°: 4) | 1700 |
| Non-complementary target (SEQ. ID N°: 5) | 5000 |

FIG. 2 and the results of table 1 show that enzymatic activity (in nmol of oxidized NADH/min) decreases strongly as and when the number of complementary bases of the target oligonucleotide increases, since it drops from 1700 to 200 nmol oxidized NADH/min when the number of complementary bases increases from 14 to 20.

If the oligonucleotide probe is used alone, the enzymatic activity obtained is 5000 to 5800 nmol/min.

EXAMPLE 3

In this example, the variation in intensity of NADH fluorescence is determined in the presence of flavin reductase and the ISIS probe alone labeled with flavin, and in the presence of the ISIS probe labeled with the flavin hybridized to the complementary oligonucleotide ICAM-20.

Figure 3:
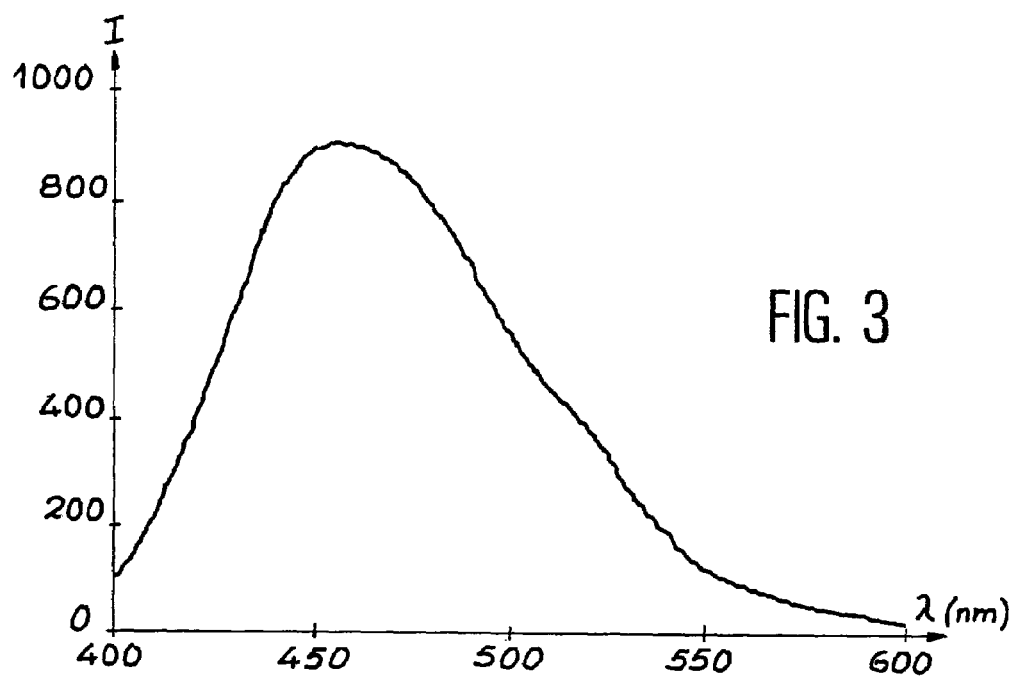
FIG. 3 shows the fluorescence emission spectrum of NADH.

FIG. 3 illustrates the fluorescence emission spectrum of NADH for an excitation at 340 nm. In this figure it is noticed that maximum emission is at 460 nm.

In this example, a total volume of 400 µl is used containing 50 mM Tris/HCl buffer, pH 7.6, 10 mM NaCl, the ISIS probe labeled with 5 µM flavin, 200 µM NADH, in the presence or not of the ICAM-20 complementary target, 50 µM, 10 equivalents.

The ISIS probe is placed in solution alone or paired with ICAM-20. NADH is then added, then the reaction is triggered at 25° C. through the addition of flavin reductase (0.3 µg per assay), i.e. 0.1 µM.

The intensity of fluorescence emission(I) of NADH is recorded in relation to time t (in s) at 460 nm (maximum emission wavelength of NADH).

Figure 4:
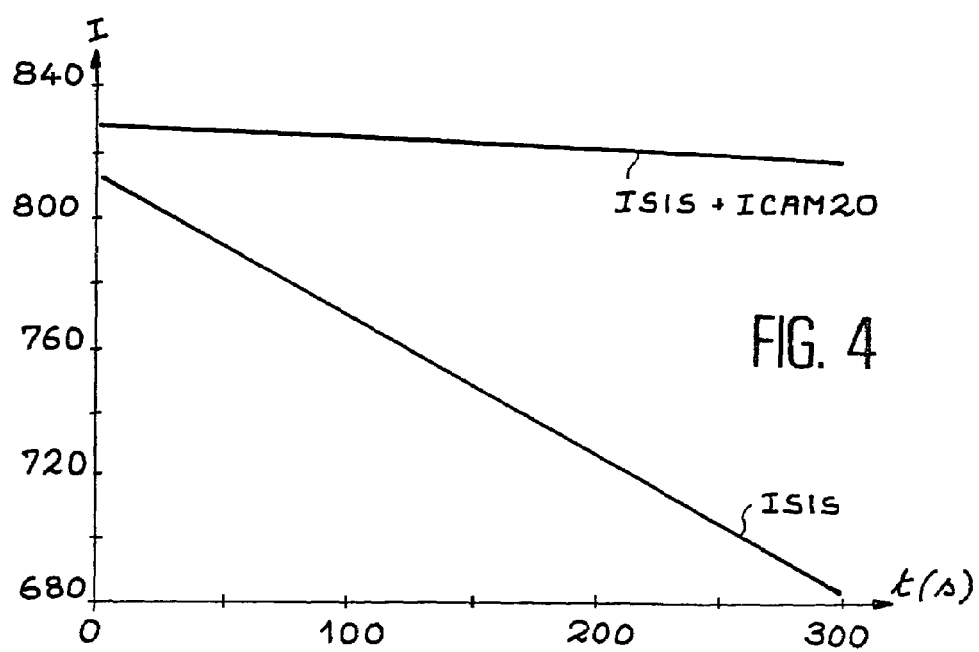
FIG. 4 illustrates the variation in intensity of NADH fluorescence in the presence of flavin reductase and of the oligonucleotide probe alone (straight line ISIS), or hybridized to a complementary target oligonucleotide (straight line ISIS+ICAM-20).

The results obtained are given in FIG. 4.

In this figure the (ISIS) straight line corresponds to the variation in fluorescence intensity for the ISIS probe alone, the (ISIS+ICAM-20) line illustrates the variation in fluorescence intensity for the ISIS probe hybridized to ICAM-20.

It is noticed in FIG. 4 that the intensity of fluorescence emission of the hybridized probe practically does not vary in relation to time.

EXAMPLE 4

Figure 5:
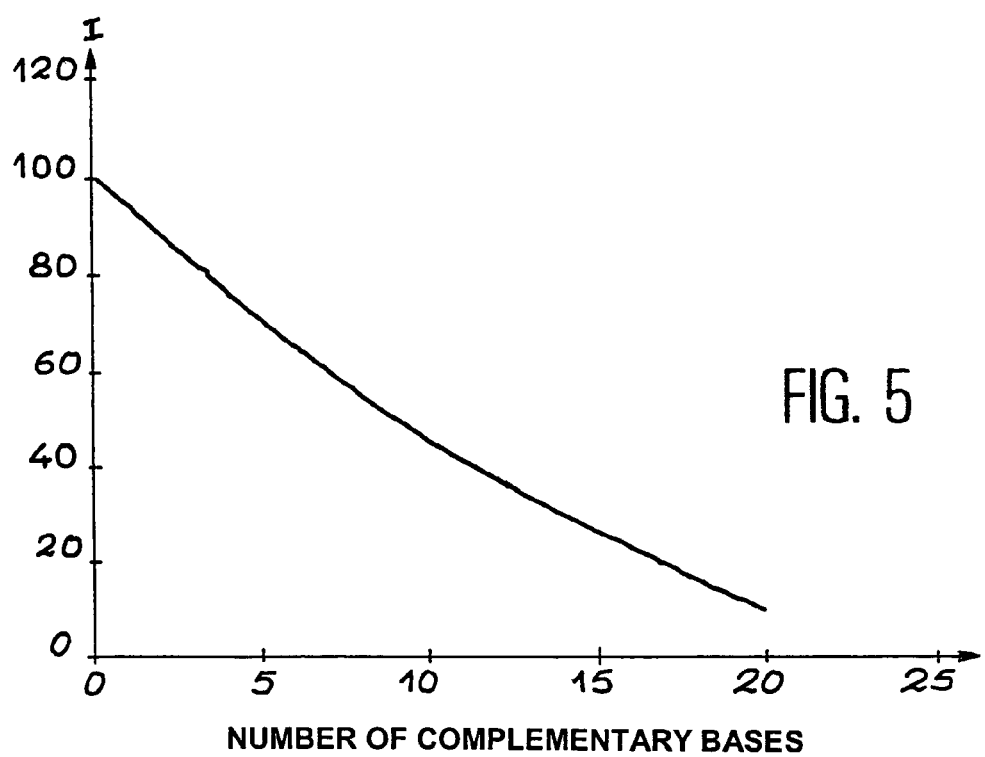
FIG. 5 illustrates the effect of the number of complementary bases of a target oligonucleotide hybridized to the oligonucleotide probe labeled with flavin, on the variation in intensity of NADH fluorescence induced by the activity of flavin reductase.

In this example, the variation in fluorescence intensity of NADH is determined in relation to the number of base pairs of the complementary target. The same operating mode is followed as in the preceding example using either target ICAM-20 or target ICAM-17 or target ICAM-14, to the proportion of 10 equivalents of target relative to the ISIS probe. The intensity I of fluorescence emission of NADH expressed in arbitrary units is recorded at 460 nm for an excitation wavelength of 340 nm, in the presence of flavin reductase in relation to time. The straight lines obtained I=f(t) are used to determine the variation in fluorescence per minute in relation to the number of associated base pairs in the formed duplex. Table 2 illustrates the variation in intensity of fluorescence emission, and FIG. 5 illustrates this variation in relation to the number of complementary bases of the target oligonucleotide. In this figure, the value 100 of the arbitrary unit represents the variation in fluorescence intensity per unit of time when ISIS is non-hybridized.

TABLE 2

| Target | Intensity of fluorescence emission (arbitrary unit) | | Enzymatic activity |
| --- | --- | --- | --- |
| | I (t = 0) | I (t = 5 min) | |
| Without | 828 | 688 | 100% |
| ICAM-20 | 828 | 814 | 10% |

TABLE 2-continued

| Target | Intensity of fluorescence emission (arbitrary unit) | | Enzymatic activity |
| --- | --- | --- | --- |
| | I (t = 0) | I (t = 5 min) | |
| ICAM-17 | 828 | 809 | 20% |
| ICAM-14 | 828 | 803 | 30% |

If the results obtained in FIG. 5 are compared with those in FIG. 2 in which optical density was measured, it can be seen that the results obtained are similar.

EXAMPLE 5

In this example the enzymatic activity of flavin reductase is determined using increasing concentrations of ISIS probe labeled with flavin. The experiment is performed in the absence of complementary oligonucleotides, using a solution of 50 mM Tris buffer, pH 7.6, 50 mM NaCl, 200 µM NADH and 0.05 g/l flavin reductase. The quantities of ISIS probe used range from 0 to 7 µM.

Figure 6:
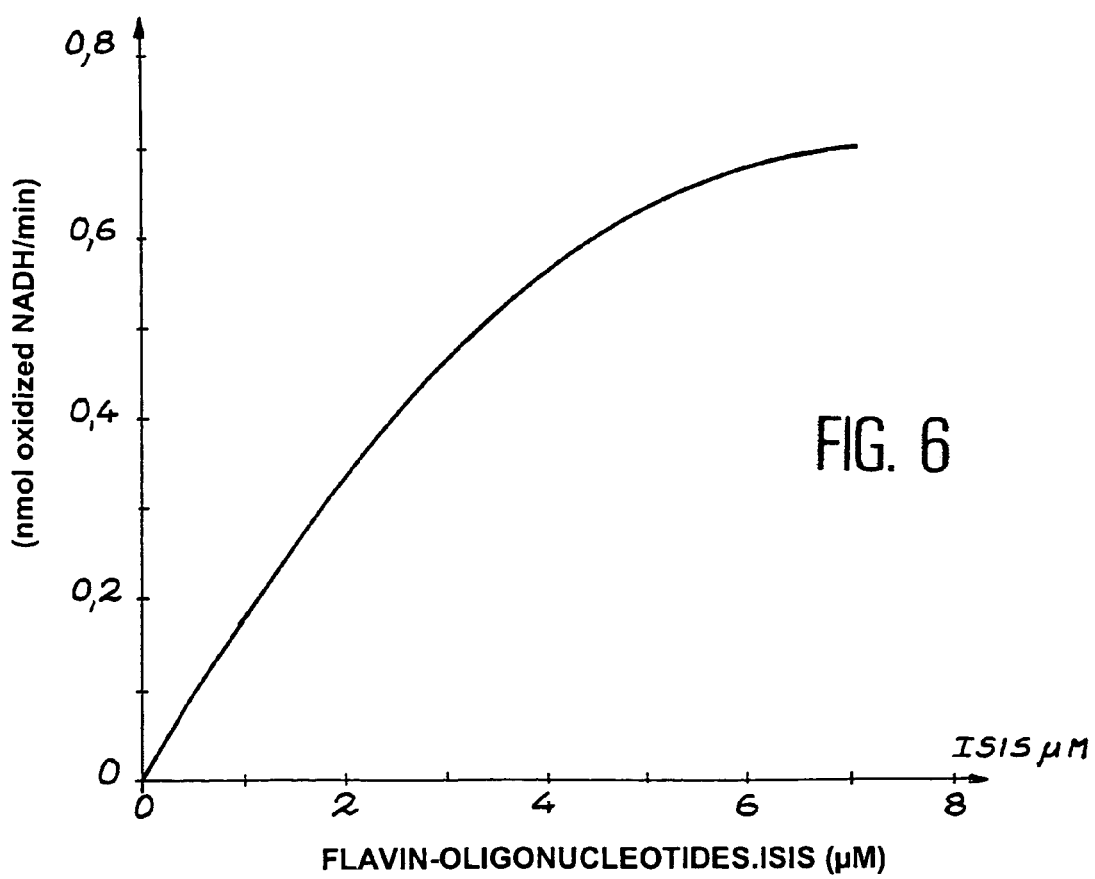
FIG. 6 illustrates the enzymatic activity of flavin reductase in relation to increasing quantities of flavin-labeled probes.

FIG. 6 illustrates enzymatic activity, i.e. the number of nanomoles of NADH oxidized per minute, in relation to the concentration (in µM) of ISIS probe. It is noticed that the enzymatic activity increases with ISIS probe concentration, i.e. flavin concentration.

CITED REFERENCES

[1] U.S. Pat. No. 5,925,525,
[2] U.S. Pat. No. 5,482,832
[3] C. Frier et al., J. Org. Chem., 62, 1997, p. 3520-3528,
[4] J. Fisher et al., Biochemistry, 1976, 15, p. 1054-1063,
[5] F. Fieschi et al., J. Biol. Chem., 1995, 270, p. 20392-20400,
[6] Scott et al., J. Am. Chem. Soc., 92:3, 11 Feb. 1970, p. 687 to 695,
[7] Hastings et al., Advances in Microbial Physiology, vol. 26, 1085, p. 235-291
[8] Zenno et al., J. Bacteriol., 1994, p. 3536-3543.

The invention claimed is:

1. A method for analyzing biological targets of DNA or RNA type, which comprises the following steps:
   a) contacting the targets to be analyzed with oligonucleotide probes labeled with a cofactor A of an enzyme E, the cofactor being such that it is recognized by enzyme E when it is fixed onto a free oligonucleotide and is less recognized by enzyme E when the oligonucleotide on which it is fixed is hybridized with a complementary oligonucleotide;
   b) adding, to the reaction medium, enzyme E corresponding to cofactor A and a substrate S of enzyme E, substrate S being converted by enzyme E into a compound C;
   c) measuring a signal representative of the activity of enzyme E on substrate S; and
   d) comparing the signal with the signal obtained when the oligonucleotide probes, labeled with cofactor A, are contacted with enzyme E and substrate S, under the same conditions, but in the absence of the targets, the difference between the two signals indicating the presence of complementary targets of the oligonucleotide probes.

2. The method according to claim 1, wherein cofactor A is no longer or almost no longer recognized by enzyme E when the oligonucleotide probes labeled with cofactor A are hybridized with complementary biological targets.

3. The method according to claim 2, wherein the signal measured in step c) represents no more than 50% of the signal obtained in the absence of biological targets.

4. The method according to claim 1, wherein the signal representative of the enzymatic activity of enzyme E on substrate S is an optic signal.

5. The method according to claim 1, wherein enzyme E and cofactor A are such that cofactor A does not fix itself onto enzyme E by covalent bond.

6. The method according to claim 1, wherein enzyme E is such that its substrate S or conversion compound C of the substrate S is used to determine the enzymatic activity of enzyme E by a variation in the light absorbing or fluorescence properties due to consumption of substrate S or production of compound C.

7. The method according to claim 5, wherein cofactor A is flavin or one of its derivatives.

8. The method according to claim 7, wherein the enzyme is a flavoprotein.

9. The method according to claim 8, wherein enzyme E is a flavin reductase or a NAD(P)H oxydase and substrate S is NADPH or NADH.

10. The method according to claim 9, wherein the signal measured is the intensity of NADH fluorescence at 460 nm or the light absorption of NADH at 340 nm.

11. The method according to claim 1, wherein cofactor A being is flavin, enzyme E is a flavin reductase and substrate S is NADH or NADPH, the signal representative of the activity of enzyme E is obtained by using a second enzyme and an aldehyde, the second enzyme being able to catalyze the reaction of the flavin reduced with the aldehyde and oxygen, the reaction being accompanied by luminescence representative of the activity of enzyme E.

12. The method according to claim 11, wherein the second enzyme is luciferase.

13. The method according to claim 1, wherein the comparison of the two signals enables determination of the extent of complementarity between the target and the oligonucleotide probe labeled with cofactor A.

14. The method according to claim 1, wherein the quantities of substrate used are such that the signal representative of the activity of enzyme E is amplified.

15. The method according to claim 1, wherein the oligonucleotide probes labeled with cofactor A are fixed onto a solid support.

* * * * *

UNITED STATES PATENT AND TRADEMARK OFFICE
CERTIFICATE OF CORRECTION

| | | |
|---|---|---|
| PATENT NO. | : 7,220,543 B2 | Page 1 of 1 |
| APPLICATION NO. | : 10/484178 | |
| DATED | : May 22, 2007 | |
| INVENTOR(S) | : Jean-Luc Decout, Marc Fontecave and Cécile Dueymes | |

It is certified that error appears in the above-identified patent and that said Letters Patent is hereby corrected as shown below:

ON THE TITLE PAGE:

The city of residence for the second inventor "Saint Ismien" should be --Saint Ismier--.

IN THE CLAIMS:

Column 12, line 64, "being is flavin" should read --is flavin--.

Signed and Sealed this

Fourth Day of September, 2007

JON W. DUDAS
*Director of the United States Patent and Trademark Office*

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: synthetic sequence

<400> SEQUENCE: 1
ctctcccctt caccacccc        20

<210> SEQ ID NO 2
<211> LENGTH: 42
<212> TYPE: DNA
<213> ORGANISM: Artificial Sequence
<220> FEATURE:
<223> OTHER INFORMATION: synthetic sequence

<400> SEQUENCE: 2

```
gcctgatgag aggggaagtg gtggggggaga catagcccca cc                42

<210> SEQ ID NO 3
<211> LENGTH: 42
<212> TYPE: DNA
<213> ORGANISM: Artificial Sequence
<220> FEATURE:
<223> OTHER INFORMATION: synthetic sequence

<400> SEQUENCE: 3
gcctgatgag aggggaagtg gtggcccaga catagcccca cc                 42

<210> SEQ ID NO 4
<211> LENGTH: 42
<212> TYPE: DNA
<213> ORGANISM: Artificial Sequence
<220> FEATURE:
<223> OTHER INFORMATION: synthetic sequence

<400> SEQUENCE: 4
gcctgatgag aggggaagtg gattcccaga catagcccca cc                 42

<210> SEQ ID NO 5
<211> LENGTH: 45
<212> TYPE: DNA
<213> ORGANISM: Artificial Sequence
<220> FEATURE:
<223> OTHER INFORMATION: synthetic sequence

<400> SEQUENCE: 5
ctcatcgtgt aaaaaaaaaa aggcagtact ggaagggcta attct              45
```